United States Patent [19] [11] 4,378,345
Okumura et al. [45] Mar. 29, 1983

[54] HAIR SETTING COMPOSITION

[75] Inventors: Takeo Okumura, Sakura; Hiroshi Ando, Funabashi, both of Japan

[73] Assignee: Kao Soap Co., Ltd., Tokyo, Japan

[21] Appl. No.: 300,559

[22] Filed: Sep. 9, 1981

[30] Foreign Application Priority Data

Sep. 19, 1980 [JP] Japan ................. 55-130322

[51] Int. Cl.³ .............. A61L 9/04; A61K 7/09; A61K 7/11
[52] U.S. Cl. ........................ 424/45; 424/71; 424/DIG. 2
[58] Field of Search ............... 424/70, 71, 72, DIG. 2, 424/45

[56] References Cited

U.S. PATENT DOCUMENTS

| | | | |
|---|---|---|---|
| 2,309,722 | 2/1943 | Wilkes et al. | 424/70 |
| 3,461,073 | 8/1969 | Crowell et al. | 424/70 |
| 4,048,301 | 9/1977 | Papantoniou | 424/70 |
| 4,165,367 | 8/1979 | Chakrabarti | 424/70 |

Primary Examiner—Donald B. Moyer
Attorney, Agent, or Firm—Oblon, Fisher, Spivak, McClelland & Maier

[57] ABSTRACT

The specification describes a hair setting composition comprising as an effective component polyethylene glycol having an average molecular weight of 6,000–30,000. It also describes a hair setting composition comprising as effective components the following ingredients: (A) polyethylene glycol having an average molecular weight of 6,000–30,000 and (B) a divalent or trivalent metal salt of pyrrolidonecarboxylic acid and/or a polyoxyalkylene-added silicone oil. Such hair setting compositions may be formulated into an aerosol type or lotion or pump spray type and facilitates long-lasting hair styling without damaging hair.

13 Claims, No Drawings

HAIR SETTING COMPOSITION

BACKGROUND OF THE INVENTION

1. Field of the Invention

This invention relates to a hair setting composition, and more particularly, to a hair setting composition containing as an effective component polyethylene glycol having an average molecular weight of 6,000-30,000. Such a hair setting composition may be formulated into an aerosol type or lotion or pump spray type and facilitates long-lasting hair styling without damaging hair.

2. Description of the Prior Art

For the setting of hair styles in beauty saloon or at home, there are known a method in which hair is wound around curlers or rods to form curls or waves and then set a hair style by brushing and a method in which hair is washed and any excess water is wiped off, after which the hair style is set with a brush while drying the hair by a dryer. In these cases, it is general to make use of a hair setting composition.

A hair setting composition is used to facilitate setting of hair style, to keep the hair style long, and to prevent the hair from being damaged and protect it from brushing during the course of the setting of the hair style. Conventionally, setting lotions, hair sprays, hair creams, hair oils and the like have been employed for these purposes.

Setting lotions and hair sprays are primarily composed of resins such as polyvinylpyrrolidone, vinyl acetate copolymers and the like. Where these lotions or sprays are used for the setting of hair style, they show the following disadvantages though exhibiting to a certain extend holding effect of finished hair style: Hair becomes stiff or dry and is felt bad when touched; so-called flaking is caused in which the resin deposited on the hair comes off in pieces by brushing, rendering the gloss of hair poor; and the resin deposited on hair surfaces does not permit easy brushing or combing, resulting in damaged hair.

On the other hand, hair cosmetics for hair conditioning such as hair creams, hair oils and the like are mainly composed of oily ingredients such as liquid paraffin, olive oil and the like and have no drawbacks of causing stiffness, flaking and the like on hair. However, they show very little or no effects in facilitating setting of hair style and holding the finished hair style as required for the hair setting composition.

As described above, none of conventionally available setting lotions, hair sprays, hair creams and hair oils have been found satisfactory as hair setting compositions. Though the mechanism of developing the setting effect of hair has not been completely solved, its principal concept is considered to be as follows. That is, the physical and chemical action of water takes an effective part in the formation of hair style. When hair is wetted, the hydrogen bonds in keratin of hair are broken. Then, when hair is styled by a hair dryer or brush or is wound using curlers or rods, hydrogen bonds are formed at locations different from the previous ones and the hair style is thus set.

In this connection, however, where hair is set by the use of water alone, the hair style gradually gets out of shape through the absorption of water by the hair and by gravity as time goes on and does not last long time, thus needing use of a certain hair setting composition. Thus, the present inventors have made an intensive study to provide a hair setting composition which meets the above requirements. As a result, it has been found that polyethylene glycol of a specific type shows excellent effects in facilitating hair styling and keeping it without damaging the hair and that such effects are synergistically increased when using it in combination with a divalent or trivalent metal salt of pyrrolidonecarboxylic acid and/or a polyoxyalkylene-added silicone oil, thus arriving at the completion of the present invention.

SUMMARY OF THE INVENTION

Accordingly, the present invention relates, according to a first aspect thereof, to a hair setting composition comprising as an effective component polyethylene glycol having an average molecular weight of 6,000-30,000 and, according to a second aspect thereof, to a hair setting composition which comprises as its effective components polyethylene glycol having an average molecular weight of 6,000-30,000 and a divalent or trivalent metal salt of pyrrolidonecarboxylic acid and/or a polyoxyalkylene added silicone oil.

DETAILED DESCRIPTION OF THE PREFERRED EMBODIMENTS OF THE INVENTION

The polyethylene glycol used in the present invention is one which has an average molecular weight of 6,000-30,000, preferably 10,000-25,000 but whose preparation is not limited to any specific one. Where a polyethylene glycol having a molecular weight smaller than its lower limit defined above is used, not only little hair setting effect is recognized, but also the composition shows a great hygroscopicity under high humidity conditions, thus lowering the holding effect of the hair style. On the other hand, where a polyethylene glycol with a molecular weight higher than the upper limit defined above is employed, hair-styling is easy and its retentivity is excellent, but the flaking occurs when brushed or combed, resulting in poor feeling to the touch.

The hair setting composition according to the invention is prepared by dissolving the above effective component is an aqueous solvent such as water, ethyl alcohol, isopropyl alcohol or the mixture of them.

In the first and second aspects of the invention, the amount of the polyethylene glycol in the hair setting composition is in the range of 0.05-5 wt% (hereinafter referred to simply as %), preferably 0.1-3%, of the total composition. Lesser amounts do not show the hair setting effect whereas larger amounts result in occurrence of the flaking problem when brushed or combed and thus poor feeling to the touch.

The polyethylene glycol used in the present invention does not render hair stiff or dry when applied and shows a very excellent hair-holding effect even under high humidity conditions, different from previously employed resins such as polyvinylpyrrolidone, vinyl acetate copolymers and the like. In addition, its setting effect is remarkably superior to that of compounds such as polypropylene glycol with the same level of molecular weight, polyvinyl alcohol and the like.

In accordance with the second aspect of the present invention, the divalent or trivalent metal salt of pyrrolidonecarboxylic acid is used in combination with the polyethylene glycol, examples of which include its calcium salt, magnesium salt, zinc salt, aluminium salt, iron salt, tin salts and the like. Of these, the aluminium salt is most preferable. The divalent or trivalent metal salt of pyrrolidonecarboxylic acid may be used in an amount of 0.01-3%, preferably 0.02-2% of the composition.

Any amount less than 0.01% of the divalent or trivalent metal salt of pyrrolidonecarboxylic acid is too little to show its effect, whereas any amount exceeding 3% is disadvantageous in that its wetness-retaining effect is imparted so much that the hair becomes sticky after application of the composition and that the hair setting retentivity becomes poor under high humidity conditions.

The polyalkylene-added silicone oil to be used in the invention is preferably a polyoxyethylene-added silicone oil represented by the following general formula (I)

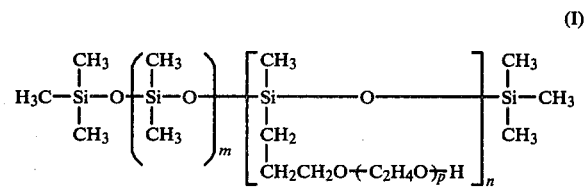

(in which m is a value of 1-10, n is a value of 10-50, and p is a value of 3-50), or a polyoxyethylene.polyoxypropylene-added silicone oil represented by the general formula (II)

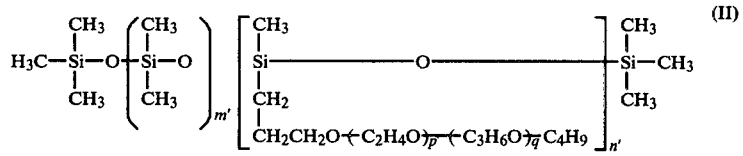

(in which m' is a value of 5-50, n' is a value of 1-10, and p' and q' are, each, a value of 10-50).

The polyoxyalkylene-added silicone oil may generally be used in an amount of 0.1-5%, preferably 0.2-4%, of the composition.

Any amount lower than 0.1% is too little to show its effect whereas any amount higher than 5% is not favorable to the touch since the hair is dressed heavily and oilily.

The hair setting composition according to the invention may further comprise, aside from the above-described components and within limited ranges of not impeding the effects of the invention, arbitrary components depending on purposes such as, for example, an oily substance such as a higher alcohol, higher fatty acid ester or the like, a nonionic surface active agent serving as an emulsifier or dissolving agent such as polyoxyethylene lauryl ether, monolauric acid polyoxyethylene sorbitan, polyoxyethylene hardened caster oil or the like, a humidifier such as glycerine, propylene glycol or the like, fragrance and colorant.

The hair setting composition according to the invention may be applied directly to the hair as it is or may be sprayed by a pump sprayer or the like, or may be filled in a container together with a propellant gas such as a FREON gas, liquefied petroleum gas, carbon dioxide gas or the like and then applied in the form of aerosol or foam.

The present invention will be described in detail by way of examples, which should not be construed as limiting the present invention thereto.

EXAMPLE 1

A hair setting composition of the following formulation was prepared to check its feeling to the touch, flaking, and hair style-retaining effect. The evaluations of the respective checking items were based on the following standards in which, regarding the feeling and flaking, a mixed solution of ethyl alcohol-water (30:70) was used as a control. The test results are shown in Table 1.

| (Composition) | |
|---|---|
| Ethyl alcohol | 30% |
| Water | 69% |
| High molecular compound | 1% |
| (See, Table 1) | |

(Evaluation Standards)

(1) Feeling to the touch

Model wigs (150 g) made of hair of Japanese females were each washed as usual using 15 g of a commercially available plain shampoo and then applied with 5 g of the hair setting composition, followed by combing the hair 5 times and setting by the use of a commercially available nylon brush and hair dryer (500 W). Sensory evaluation for the touch of the wigs was conducted by a panel of ten female members trained for the purpose.

The average of the values of evaluation given by the panel members represents the feeling of touch.

| Value of Evaluation | Significance |
|---|---|
| +2 | Better than standard. |
| +1 | Slightly better than standard. |
| 0 | Equal to standard. |
| −1 | Slightly poorer than standard. |
| −2 | Poorer than standard. |

(2) Flaking

The model wigs evaluated in (1) were combed 20 times with a commercially available nylon brush to determine whether or not the flaking took place. The letter "x" indicates where the flaking occurred while the letter "o" designates where no flaking occurred.

(3) Holding Effect of Hair Style

Bundles of hair with a length of 20 cm and a weight of 5 g made of hair of Japanese females were each washed with a commercially available plain shampoo and any excess water was removed by towel. The hair setting compositions were each applied uniformly on the bundle in an amount of 0.5 g and the bundle was combed twice and then wound around a curler of 2 cm in diameter, followed by air-drying overnight and removing from the curler next day. After having been allowed to stand at 20° C. in a relative humidity of 80% for 1 hour, the bundle was measured to determine its apparent length and this value was evaluated as the hair style retaining effect.

Smaller valves show a better hair style retaining effect since the curling has been maintained tighter.

TABLE 1

| | | (Results) | | |
|---|---|---|---|---|
| | High molecular compound | Feeling to the touch | Flaking | Hair style retaining effect |
| Invented Composition | Polyethylene glycol (molecular weight 6000) | 0 | o | 13.4 |
| | Polyethylene glycol (molecular weight 20000) | 0 | o | 12.0 |
| | Polyethylene glycol (molecular weight 30000) | 0 | o | 12.2 |
| Comparative Composition | Polyethylene glycol (molecular weight 4000) | 0 | o | 16.0 |
| | Polyethylene glycol (molecular weight 50000) | −0.7 | x | 13.3 |
| | Vinylpyrrolidone/ vinyl acetate copolymer | −0.9 | x | 13.6 |
| | Acrylic acid/ methacrylic acid ester copolymer | −1.1 | x | 13.0 |
| Control | Water | — | — | 17.0 |

EXAMPLE 2

Various hair setting compositions of the invention in which a polyoxyalkylene-added silicone oil and/or a pyrrolidone-carboxylic acid had been added as shown in Table 2 were compared in effects with a commercially available hair cream setting lotion and hair spray.

The results are shown in Table 3.

TABLE 2

| | Hair setting composition A | Hair setting composition B | Hair setting composition C | Hair setting composition D | Hair setting composition E | Hair setting composition F |
|---|---|---|---|---|---|---|
| Polyethylene glycol (molecular weight 20,000) | 1 | 1 | 1 | 1 | 1 | 1 |
| Ethyl alcohol | 30 | 30 | 30 | 30 | 30 | 30 |
| Water | 69 | 68 | 68.5 | 68.5 | 68.5 | 67.5 |
| Polyoxyethylene-added silicone oil (in formula (I), n = 20, m = 3, and p = 10) | — | 1 | — | — | — | 1 |
| Aluminium monohydroxydi-pyrrolidonecarboxylate | — | — | 0.5 | — | — | 0.5 |
| Sodium pyrrolidonecarboxylate | — | — | — | 0.5 | — | — |
| Zinc dipyrrolidonecarboxylate | — | — | — | — | 0.5 | — |

TABLE 3

| | Feeling to the touch* | Easiness to comb* | Hair style retaining effect |
|---|---|---|---|
| Hair setting composition A | — | — | 12.2 |
| Hair setting composition B | +1.0 | +1.3 | 12.0 |
| Hair setting composition C | +0.8 | +0.5 | 12.1 |
| Hair setting composition D | −0.6 | −0.1 | 13.5 |
| Hair setting composition E | +0.8 | +0.5 | 12.0 |

TABLE 3-continued

| | Feeling to the touch* | Easiness to comb* | Hair style retaining effect |
|---|---|---|---|
| Hair setting composition F | +1.5 | +1.4 | 11.8 |
| Commercially available hair cream | +0.8 | +0.8 | 16.2 |
| Commercially available setting lotion | −1.2 | −1.8 | 13.0 |
| Commercially available hair spray | −1.3 | −1.9 | 13.5 |

*The feeling to the touch and easiness to comb were determined as follows: the hair setting composition A was taken as standard and the other compositions were evaluated in comparison with the composition A according to the evaluation standard of Example 1.

EXAMPLE 3

(a) Aerosol type hair setting composition:

| (Formulation) | |
|---|---|
| (1) Polyethylene glycol (molecular weight 20,000) | 1.0 (parts by wt.) |
| (2) Polyoxyethylene.polyoxy-propylene-added silicone oil (in formula (II), m' = 20, p' = 20, q = 20, and n' = 5) | 1.0 |
| (3) Fragrance | 0.1 |
| (4) Water | 10.0 |
| (5) Absolute ethanol | 23.2 |
| (6) FREON 12 | 50.0 |

(Preparation)

To an aqueous solution of (1) dissolved in (4) was added an ethanol solution obtained by dissolving (2) and (3) in (5), which was packed in an aerosol can and FREON 12 was also filled in the can.

(b) Lotion type/pump type hair setting composition:

| (Formulation) | |
|---|---|
| (1) Polyethylene glycol (molecular weight 13,000) | 2.0 (parts by weight) |
| (2) Aluminium monohydroxy-dipyrrolidonecarboxylate | 0.1 |
| (3) Polyoxyethylene-added silicone oil (in formula (I), n = 20, m = 5 and p = 10) | 1.0 |
| (4) Polyoxyethylene lauryl ether (added with 20 moles of ethylene oxide) | 0.5 |

| (Formulation) | |
|---|---|
| (5) Fragrance | 0.1 |
| (6) Colorant | As needed |
| (7) Absolute ethanol | 40.0 |
| (8) Water | Balance |

(Preparation)

To an aqueous solution obtained by dissolving (1) and (2) in (8) was added an ethanol solution obtained by dissolving (3), (4), (5) and (6) in (7). The solution was packed in a bottle thereby obtaining a lotion-type or pump-type hair setting composition.

The hair setting compositions obtained in (a) and (b) were sprayed over hair which had been washed and dried with towel, and the hair style was set using a dryer and a nylon brush, the thus-set hair showed no stiffness and excellent set-retentivity.

It will be understood that the preceding examples have been given for illustration purposes only and that this invention is not limited to the specific embodiments disclosed therein. It will, on the other hand, be readily apparent to those skilled in the art that many variations can be made in the polyethylene glycol, divalent or trivalent metal salt of pyroolidonecarboxylic acid, the polyoxyalkylene-added silicone oil and proportions of ingredients within the limits set forth without departing from the spirit or scope of this invention, defined in the appended claims.

What is claimed is:

1. A hair setting composition, comprising:
(A) polyethylene glycol having an average molecular weight of 6,000–30,000; and
(B) a calcium, magnesium, zinc, aluminum, iron, or tin salt of a pyrrolidone carboxylic acid or a polyoxyalkylene-added silicone oil represented by the formula

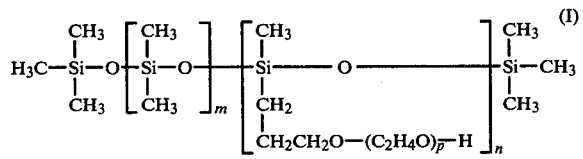

in which m has a value of 1–10, n has a value of 10–50, and p has a value of 3–50, or by the formula

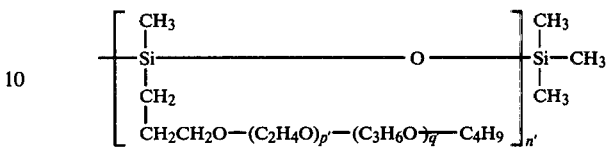

in which m' has a value of 5–50, n' has a value of 1–10, and p' and q' each has a value of 10–50.

2. A hair setting composition according to claim 1, wherein said composition is an aqueous solution containing 0.05–5 wt% of said polyethylene glycol, and 0.01–3 wt% of the salt of pyrrolidonecarboxylic acid or 0.1–5 wt% of the polyoxyalkylene-added silicone oil.

3. A hair setting composition according to claim 2, wherein the salt of pyrrolidonecarboxylic acid and the polyoxyalkylene-added silicone oil are present respectively in amounts of 0.02–2 wt% and 0.2–4 wt% of the composition.

4. A hair setting composition according to claim 2, wherein the aqueous solution contains a lower alkyl alcohol.

5. A hair setting composition according to claim 1, wherein the polyethylene glycol has an average molecular weight of 10,000–25,000.

6. A hair setting composition according to claim 1, wherein the polyethylene glycol is present in an amount of 0.1–3 wt% of said composition.

7. A method of setting hair, comprising the step of: contacting human hair with a solution containing polyethylene glycol having an average molecular weight of 6,000–30,000 in an amount of 0.05–5 weight percent of the solution.

8. The method of claim 7, wherein the polyethylene glycol has an average molecular weight of 10,000–25,000.

9. The method of claim 7, wherein the polyethylene glycol is present in an amount of 0.1–3 weight percent of the solution.

10. The method of claim 7, wherein said solution is aqueous.

11. The method of claim 10, wherein the aqueous solution contains a lower alkyl alcohol.

12. The method of claim 11, wherein the alcohol is a $C_1$–$C_3$ alcohol.

13. The method of claim 12, wherein the alcohol is ethanol or isopropanol.

* * * * *